United States Patent
Langley et al.

[11] Patent Number: 5,460,817
[45] Date of Patent: Oct. 24, 1995

[54] PARTICULATE COMPOSITION COMPRISING A CORE OF MATRIX POLYMER WITH ACTIVE INGREDIENT DISTRIBUTED THEREIN

[75] Inventors: John G. Langley, Leeds; Kenneth C. Symes, Keighley; Kishor K. Mistry, Bradford; Peter Chamberlain, Shipley, all of Great Britain

[73] Assignee: Allied Colloids Ltd., United Kingdom

[21] Appl. No.: 30,830

[22] Filed: Mar. 12, 1993

Related U.S. Application Data

[63] Continuation-in-part of Ser. No. 749,695, Aug. 26, 1991, Pat. No. 5,194,263, which is a continuation-in-part of Ser. No. 467,668, Jan. 19, 1990, abandoned, and a continuation-in-part of Ser. No. 734,545, Jul. 23, 1991, Pat. No. 5,324,445, and a continuation-in-part of Ser. No. 398,083, filed as PCT/GB92/00867, May 14, 1991, abandoned.

[30] Foreign Application Priority Data

| Jan. 19, 1988 | [GB] | United Kingdom | 8901182 |
| Aug. 24, 1988 | [GB] | United Kingdom | 8820061 |
| Aug. 24, 1988 | [GB] | United Kingdom | 8820062 |
| Jan. 20, 1989 | [GB] | United Kingdom | 8901254 |
| May 14, 1991 | [GB] | United Kingdom | 9110408 |
| Aug. 2, 1991 | [GB] | United Kingdom | 9116682 |

[51] Int. Cl.⁶ ................................. A01N 25/26
[52] U.S. Cl. ................. 424/408; 252/90; 252/174.12
[58] Field of Search .......................... 424/405, 408; 514/774; 252/90, 174.12

[56] References Cited

U.S. PATENT DOCUMENTS

| 3,691,090 | 9/1972 | Kitajima et al. | 252/316 |
| 3,838,007 | 9/1974 | van Velzen | 195/31 |
| 4,090,973 | 5/1978 | Maguire, Jr. et al. | 252/89 R |
| 4,233,057 | 11/1980 | Lavanish | 71/90 |
| 4,303,642 | 12/1981 | Kangas | 514/89 |
| 4,589,914 | 5/1986 | Cartwright | 71/103 |
| 4,677,003 | 6/1987 | Redlich et al. | 427/373 |
| 4,758,670 | 7/1988 | Muller | 71/92 |
| 4,777,089 | 10/1988 | Takizawa et al. | 428/402.22 |
| 4,801,544 | 1/1989 | Munk | 435/188 |
| 4,898,781 | 2/1990 | Onouchi et al. | 428/402.22 |
| 4,906,396 | 3/1990 | Falholt et al. | 252/174.12 |
| 5,043,163 | 8/1991 | Pap | 424/405 |
| 5,123,950 | 6/1992 | Homma et al. | 424/405 |
| 5,137,646 | 8/1992 | Schmidt et al. | 252/8.8 |
| 5,281,357 | 1/1994 | Morgan et al. | 252/174.13 |
| 5,292,533 | 3/1994 | McMahon et al. | 424/405 |

FOREIGN PATENT DOCUMENTS

| 0351162 | 7/1989 | European Pat. Off. . |
| 0379379 | 1/1990 | European Pat. Off. . |
| 254244 | 5/1985 | Japan . |
| 105098 | 5/1988 | Japan . |
| 1475229 | 6/1977 | United Kingdom . |
| 1507739 | 4/1978 | United Kingdom . |

OTHER PUBLICATIONS

CA 107,98645.

Primary Examiner—Thurman K. Page
Assistant Examiner—W. Benston
Attorney, Agent, or Firm—Ostrolenk, Faber, Gerb & Soffen

[57] ABSTRACT

A particulate composition comprises particles having a substantially anhydrous core comprising an active ingredient. Generally the core comprises a matrix polymer with the active ingredient distributed throughout this. Generally there is an outer protection shell of polymer, generally formed by coacervation. The invention is a value for the production of powders, dispersions in non-aqueous liquids (for instance when the active ingredient is a detergent enzyme) and dispersions in water (for instance when the active ingredient is an agrochemical.

8 Claims, No Drawings

PARTICULATE COMPOSITION COMPRISING A CORE OF MATRIX POLYMER WITH ACTIVE INGREDIENT DISTRIBUTED THEREIN

RELATED APPLICATIONS

This application is a continuation-in-part of Ser. No. 07/749,095 filed Aug. 26, 1992, and now U.S. Pat. No. 5,194,263, which is a C-I-P of Ser. No. 07/467,668 filed Jan. 19, 1990, now abandoned Aug. 27, 1991 and a C-I-P of Ser. No. 07/734,545 filed Jul. 23, 1991, and now U.S. Pat. No. 5,324,445 and a C-I-P of Ser. No. 07/398,083 filed 24 Aug. 1989 now abandoned and a C-I-P of PCT/GB92/00867 published as WO92/20771 filed 14 May 1992.

BACKGROUND TO THE INVENTION

This invention relates to the production of particulate compositions containing active ingredients, for instance agriculturally useful active ingredients such as insecticide or herbicides or biologically active ingredients such as enzymes. The invention includes relatively coarse particles that can be handled as powders and fine particulate compositions which are generally in the form of liquid dispersions of the fine particles. Numerous ways of protecting active ingredients from the ambient environment are known. Some rely on a wholly liquid system. In U.S. Pat. No. 4,801,544, aqueous micelles of enzyme and surfactant are emulsified into a hydrocarbon solvent. In U.S. Pat. No. 4,906,396, enzyme is dispersed in a hydrophobic fluid, such as a silicone oil.

More usually, the enzyme is protected by a solid phase. In U.S. Pat. No. 4,090,973 solid surfactant is used. Often, however, a polymeric material is used. The enzyme or active ingredient may be dispersed in a polymeric matrix or it may be encapsulated by a polymeric shell formed around a core containing the active ingredient.

The solid polymeric material can be made by polymerisation of monomeric material in the presence of the active ingredient, but this is generally undesirable and normally the solid polymer of the matrix or shell is formed by depositing solid polymer from a solution of polymer. The polymer can remain chemically unchanged during the deposition from dissolved to solid form, the deposition being due primarily to a change in the solvent composition or properties. Alternatively, deposition can be caused by, accompanied by or followed by a chemical change in the polymer, such as neutralisation, complexing with another polymer, or cross linking. The formation of a solid polymer shell in this manner from a solution of polymeric material is generally termed coacervation.

Typical techniques for forming a polymer shell are described in, for instance, GB 1,275,712, 1,475,229 and 1,507,739, DE 3,545,803 and U.S. Pat. No. 3,591,090.

A particular problem arises when the active ingredient is an enzyme, especially an enzyme suitable for incorporation in detergents, because of the difficulty of preventing the enzyme losing activity before use.

Many different ways of encapsulating enzymes have been proposed. Some do not include coacervation. For instance GB 1,377,725 contacts atomised droplets of an aqueous slurry of enzyme with particles of starch. However there is a risk that the resultant coating will be discontinuous. It is therefore preferred to form the coating or matrix by deposition of solid polymer from a solution of polymer in which the enzyme is dispersed, i.e. by coacervation.

For instance in U.S. Pat. No. 3,838,007 droplets of enzyme dispersed in an aqueous solution of, for instance, gelatin are dispersed into water and then cross linked, to give cross linked particles of the gelatin containing the enzyme.

In JP-A-61254244 a typical process comprises mixing enzyme powder and silica into an aqueous solution of polyvinyl alcohol or other suitable polymer, dispersing the aqueous suspension into a non-aqueous liquid and adding acetone, so as to deposit the polymer as a wall around the enzyme particles. The product is said to have a particle size of around 50 to 2,000 um.

In U.S. Pat. No. 4,898,781 a dispersion is formed of enzyme powder in propylene glycol and aqueous polyvinyl alcohol and this dispersion is then converted into particles by various techniques. In one technique, the dispersion is introduced as droplets into an aqueous solution of cross linking agent, thereby solidifying by cross linking the polyvinyl alcohol. In another technique, the dispersion is dispersed into a hydrophobic solvent and then heated, so as to drive off water and solidify the polyvinyl alcohol. The products are said to have a size of 20 to 1,000 μm. Other techniques are described. JP-A-63105098 includes similar process description and many of the examples are identical. It proposed that the particles of enzyme in a covering of polyvinyl alcohol should be homogeneously dispersed in a liquid or gel detergent.

U.S. Pat. No. 5,035,900 describes processes for encapsulating enzyme or other biologically produced material in a matrix of polymeric material by mixing the polymeric material with an aqueous liquor containing the biologically produced material (as a fermentation liquor or plant extract), dispersing this mixture in a water immiscible liquid and azeotroping the dispersion. The product can either be relatively coarse beads that can be recovered or a stable dispersion of small particles in the water immiscible liquid. Although this is a very useful recovery technique and provides some protection to the enzyme, additional stabilisation is desirable.

Instead of or in addition to protecting the active ingredient from the environment, there is also a need to provide a convenient way of delivering the active ingredient to a chosen place for use, especially when the active ingredient may be toxic and/or may need to be released into the environment only at a controlled rate.

For instance when the active ingredient may have some toxicity (for instance when it is a water insoluble pesticide or other agrochemical) it is frequently necessary to formulate the compound as a concentrate that can be diluted at the point of use to form a sprayable composition. When the compound is water soluble, the concentrate can be a concentrated aqueous solution or a water soluble granule or other soluble solid. However many agriculturally useful compounds are insoluble in water. It is generally preferred that they should be applied by spraying an aqueous composition and so the concentrate of water-insoluble active ingredient must be stable and must be capable of easy distribution into water.

One common type is a wettable powder in which powdered insoluble material has been treated to render it wettable, but there is increasing concern about dusting and other environmental problems associated with traditional wettable powders.

Another type is a dispersible paste or cream, usually referred to as a "flowable". This can readily be diluted with water and is reasonably satisfactory for many active ingredients. However a problem with both flowables and wettable powders is that the active ingredient has to be produced in the form of particles of a desired small size and this can be difficult or impossible with some materials, especially some agrochemicals. For instance these formulations are not appropriate when the active ingredient is a liquid or when it is a relatively low melting solid, for instance a solid that melts at below 80° C., because of the difficulty of making the active ingredient in this fine particulate form.

Water insoluble liquids and low melting solids can be formulated as emulsifiable concentrates but it is now frequently considered desirable to avoid this type of formulation for environmental reasons associated with, for instance, the organic solvent that is generally present in such concentrates.

It would therefore be desirable to be able to provide an active ingredient in the form of a particulate composition which is readily dilutable by water, is substantially free of organic solvent or dusting problems, and gives a satisfactory rate of release of the active ingredient.

It is already well known to use polymeric materials in the formulation of various active ingredients. Thus it is known to diffuse a low melting or liquid active ingredient into a preformed polymeric matrix (e.g., as in U.S. Pat. No. 4,303,642) or to encapsulate an active ingredient in beads by forming an emulsion or dispersion in water of polymerisable material and the active ingredient and then polymerising the polymerisable material. The product will, depending upon the materials and process conditions, be in the form of either a particulate matrix throughout which the active ingredient is distributed or small (or large) capsules comprising a shell of polymeric material around a core containing the active ingredient.

Although these diffusion and polymerisation techniques are useful in some instances, they are relatively expensive and this is justified only because they are designed primarily to provide controlled release of an active ingredient. They are not appropriate to the more fundamental problem of providing an improved way of formulating a wide range of water insoluble agrochemical or other active ingredients in an economic manner in the form of environmentally satisfactory concentrates that can readily be diluted with water to form sprayable compositions.

STATEMENT OF THE INVENTION

In one of its aspects, the invention provides a particulate composition that comprises particles having a substantially anhydrous core comprising a matrix polymer and an active ingredient distributed through the matrix polymer and an outer protective shell of polymer. Such a composition can be in the form of a powder of relatively coarse particles (e.g. 50 µm) or a liquid dispersion of fine particles, e.g. below 20 µm and often below 10 µm, dispersed in a liquid.

When improved protection is required, it is preferred that the particles should also comprise a hydrophobic material between the matrix and the shell. Preferably the hydrophobic material is an oil and the solid matrix polymer is sufficiently hydrophobic that it will partition preferentially into the oil rather than into water. This provides particularly useful impermeability against the migration of moisture into the particles and so is of particular value in, for instance, liquid compositions wherein the active ingredient is a detergent enzyme.

Another particulate composition according to the invention comprises particles having a substantially anhydrous core comprising a matrix polymer that is a substantially free-base of a cationic, substantially water insoluble polymer that can be solubilised by conversion to to an ionic form by acid addition or quaternisation. Again, this is of particular value when the active ingredient is a detergent enzyme, and especially when the composition is a liquid composition containing such particles. Further improvement in protection is achieved when the particles comprise hydrophobic material between the matrix and the shell, as described above.

The invention also provides agricultural concentrates, and sprayable compositions obtainable by dilution of the concentrates with water, wherein the composition is a substantially stable dispersion in an aqueous medium of particles that are substantially all below 10 µm in size and that each comprise a core enclosed within a polymer shell, wherein the core comprises a water insoluble agrochemical selected from the group consisting of herbicides, semiochemicals, pesticides, plant growth regulators and nutrients, and the core also comprises polymeric matrix generally in an amount of at least 20% by weight based on the weight of agrochemical.

In all of these compositions, the polymeric shell can be provided in any convenient manner but it is particularly preferred that it should be provided by coacervation. Coacervation can be conducted in generally known manner using either a single coacervating polymer or a blend of coacervating polymers.

The invention also includes processes of making substantially dry particles, preferably substantially dry particulate compositions as described above. In its broadest aspect, this process comprises dispersing aqueous droplets comprising the active ingredient into a water immiscible liquid containing polymerisation stabiliser and/or water in oil emulsifier and removing water from the dispersion by distillation. Preferably water is removed as an azeotrope with some of the water immiscible liquid. The polymeric stabiliser can form a protective shell, or layer, around the resultant dry particles comprising or consisting of the active ingredient. The shell of stabiliser can be formed, for example, by chemical or physical interaction at the interface between the active ingredient and the water immiscible liquid. Thus a liquid composition of substantially dry detergent enzyme particles having a size preferably below 10 µm, and most preferably below 3 µm can be formed in this manner.

When it is desired that the particles have a core comprising matrix polymer, the aqueous composition that is dispersed into the water immiscible liquid may be a film forming oil-in-water emulsion of the polymer or an aqueous solution of the polymer, preferably in the form of a salt that will decompose during the distillation. For instance the polymer may be a salt of anionic polymer which a volatile amine or a cationic polymer with a volatile acid.

When the particles are to be provided with an outer shell, they are preferably made by providing a substantially anhydrous dispersion in water immiscible liquid of particles of a matrix polymer containing active ingredient (for instance prepared as above), dispersing this substantially anhydrous dispersion into an aqueous solution of encapsulating polymeric material that can be caused to deposit as a solid shell about particles dispersed in the solution and causing a solid polymer shell to form around the droplets of the matrix particles in the water immiscible liquid. Preferably the matrix polymer partitions into the water immiscible liquid in preference to the aqueous solution of encapsulating polymeric material.

DESCRIPTION OF THE PREFERRED EMBODIMENTS

The use of a solid matrix polymer that is sufficiently hydrophobic that it will partition preferentially into the water immiscible liquid (oil) rather than into water gives improved stability.

By referring to partitioning into "water," we are referring in particular to the partitioning of the solid matrix polymer into the aqueous solution from which the shell polymer was formed. In many instances, the partitioning properties into ordinary water do, however, give a useful guide.

If the encapsulating polymer was deposited from a neutral solution, then it is more convenient to define the matrix polymer as partitioning into the oil in preference to water, but if the encapsulating polymer was mixed with the dispersion in the form of an alkaline solution then the relative partitioning effect should be determined with respect to an alkaline solution corresponding to the alkalinity of that solution in order to allow for any solubilisation of the polymer by salt formation with the alkali of the encapsulating solution.

If the matrix polymer does not partition in this manner, there may be a tendency for water from the aqueous solution of encapsulating polymer to migrate into the matrix polymer.

Since the formation of the dispersion generally involved homogenising the polymer-in-oil dispersion into the aqueous solution encapsulating polymer, the act of forming the dispersion was able to result in intimate and prolonged contact between the polymer particles and the aqueous solution.

It seems that during this contact there can be migration of water from the solution into the matrix polymer, with the result that, even though the polymer particles had been dried by azeotroping, the particles that were then encapsulated within the outer shell contained trapped moisture. This can be undesirable for enzymes and other active ingredients.

Also, there can be some migration of the enzyme or other active ingredient out of the matrix polymer and into the aqueous solution, thereby losing the benefit of trapping the enzyme initially in the matrix polymer.

Finally, because of the attraction of the aqueous solution to the matrix polymer, the encapsulating polymer could tend to deposit direct on to the matrix polymer, without any oil trapped between the matrix polymer particle and the encapsulating polymer shell. Since the oil is capable of hindering the inward migration of moisture, this also was undesirable.

In the invention, we preferably use a matrix polymer that is so hydrophobic that it partitions preferentially into the oil rather than into the aqueous solution of encapsulating polymer.

This therefore reduces the risk of moisture migrating from the aqueous solution into the matrix, and it reduces the risk of enzyme or active ingredient migrating out of the matrix into the aqueous solution. Because the aqueous solution is incompatible with both the hydrophobic oil and the matrix polymer there is increased tendency for the encapsulating shell to be formed around a layer of oil, rather than in direct contact with a matrix polymer particle. Finally, the increased hydrophobic properties of the matrix polymer reduce still further the tendency for migration of moisture into the polymer.

In a preferred process of the invention, the substantially anhydrous dispersion of particles of the matrix polymer in oil is made by providing a dispersion in oil of an aqueous solution of matrix polymeric material containing enzyme or other active ingredient, subjecting this dispersion to distillation to provide a substantially anhydrous dispersion in oil of particles of matrix polymer containing active ingredient, and during or after the distillation converting the polymer solution into a solid polymer.

The initial aqueous solution of matrix polymeric material can be made by dissolving the polymeric material in water or other aqueous solution in which it is soluble, and dispersing or dissolving the active ingredient in the solution. In another process, the dispersion is made by reverse phase polymerisation of a water soluble monomer or monomer blend in the presence of the active ingredient.

The conversion of the droplets of polymer solution into solid polymer particles can be brought about by various techniques. For instance it can be due merely to evaporation of solvent. It can be due to chemical modification even though solidification may include another cause. This modification should produce a polymer that is insoluble in water and that will partition into the oil in preference to the aqueous solution of encapsulating material.

One form of chemical modification can involve cross linking, for instance a cross linking agent can be included in the polymer solution and will cause cross linking during or after the azeotroping.

Another, and preferred, form of chemical modification comprises converting a polymer that is in salt form into free base or free acid form. Thus a polymer containing amino groups can be present initially as a water soluble salt but can be insolubilised by conversion to the free base, or polymer that is in anionic soluble salt form can be insolubilised by conversion to the free acid. Such conversion can be partial or complete. Preferably the salt forming moiety is volatile with the result that conversion to the free acid or free base can be achieved during distillation. The use of a heat decomposable derivative of a free-base, amine containing, polymer is particularly desirable since the provision of a matrix of a free-base polymer provides good stability when the active ingredient is a detergent enzyme for incorporation in a liquid detergent. However it is also satisfactory to use amine (including ammonium) salts of anionic polymer.

The chemical modification of the polymer normally occurs during or after azeotroping and renders the matrix less permeable, e.g., to liquid detergent concentrate.

Another way of converting the matrix polymer to solid form is by selecting a hydrophobic polymer from the class known as "low critical solution temperature" (LCST polymers). The process by which these can be used for the matrix is substantially the same as the process by which they can be used for forming the encapsulating shell, and this is described in more detail below. In brief, a characteristic of such polymers is that they can be insolubilised by heating to a critical temperature (for instance as can happen during the distillation stage) and a depressant for the temperature of insolubilisation (for instance a water miscible non-solvent or an electrolyte) can be added to stabilise the solid form at a lower temperature. This is all described in more detail below.

Other coacervating techniques can be used.

In this specification, and in particular in the following discussion of the formation of the polymer shell, we use the term "coacervation" and "coacervating polymer" in a general sense, namely any mechanism by which a polymer can be converted from a solution form to a solid, encapsulating, form. Accordingly, for convenience, we refer below to the encapsulating polymer as a coacervating polymer and we refer to the aqueous solution of this as an aqueous coacervating solution.

By saying that the matrix polymer partitions into the oil in preference to the aqueous solution of coacervating polymer, or other water phase, we mean that the polymer particles will be preferentially attracted to the oil phase rather than to the aqueous phase. One simple way of demonstrating whether or not the matrix polymer does preferentially partition into the oil phase is to incorporate some water soluble dye into the matrix polymer and then to disperse vigorously into the aqueous phase a dispersion of the dyed polymer particles in the oil, and then to allow the dispersion to phase separate. If substantially all the dye has remained in the polymer particles, this shows that there was substantially no contact between the polymer particles and the water, and that the polymer particles therefore partition preferentially into the oil phase. However if the water phase is significantly dyed, this shows that the polymer particles have partitioned significantly or preferentially into the aqueous phase.

The oil can be any hydrophobic, water immiscible, liquid. Examples are aliphatic, cycloaliphatic, aromatic and naphthenic oils, vegetable oils and silicone oils.

Because the oil is hydrophobic, and because the matrix polymer also is hydrophobic and is attracted to the oil in preference to the water, a film or larger amount of oil is held around each polymer particle during the formation of the coacervate, and the coacervate coating is formed as an outer shell around this inner shell of oil. This has two significant advantages:

Firstly, there is little or no direct contact between the aqueous coacervating phase and the substantially anhydrous matrix polymer. As a result, there is little or no opportunity for water to migrate into the substantially anhydrous matrix polymer during the formation of the coacervate coating or for active ingredient in the matrix polymer to migrate out into the coacervating solution. In particular, the coacervation can be conducted without raising the moisture content of the matrix polymer.

Secondly, the active ingredient in the matrix polymer is protected from its surroundings not only by the outer coacervate coating but also by the inner layer of hydrophobic oil. Thus even if the coacervate coating has a tendency to allow permeation by moisture, the inner shell of hydrophobic oil between the coacervate and the matrix polymer will reduce or eliminate any risk of transfer of moisture from outside the particle to the matrix polymer or transfer of water soluble active ingredient in the matrix polymer to outside the coacervate coating.

In order that the polymer does partition preferentially into oil, it is necessary for it to be much more hydrophobic than, for instance, the acrylic acid-ammonium acrylate polymer proposed in EP 356239.

As mentioned above, the matrix polymer is generally provided by insolubilising a polymer that was initially provided as an aqueous solution. Any modification that achieves this insolubilisation can be used but preferably the modification is reversible, so that the polymer can then be solubilised when it becomes necessary to facilitate release of active ingredient from within the particles into water. The modification can be achieved chemically or physically. When the modification is achieved chemically, the initially soluble polymer is preferably a copolymer of water soluble ionic monomer with water insoluble monomer, in which event the reversible insolubilisation will preferably comprise converting some or all of the ionic monomer groups to free acid or free base monomer groups.

Suitable monomers are ethylenically unsaturated monomers. Ionic monomers are preferably anionic monomers groups that include sulphonic or, preferably, carboxylic acid groups. Preferred monomers include methacrylic and acrylic acids. The anionic groups may be present in the soluble polymer as alkali metal or amine salts and may be converted to free carboxylic acid groups in the insolubilisation reaction. This can be achieved by acidification with hydrochloric acid or other suitable acid but preferably the anionic group is present as a salt of a volatile amine (e.g., ammonia) and the acidification is achieved by heating the polymer sufficient to volatilise the ammonia or other amine. This heating can occur during the distillation step. Although anionic groups are preferred as the ionic groups, cationic groups such as dialkylaminoalkyl (meth)-acrylate or amide acid addition or quaternary ammonium salt can be used.

The ionic groups must be copolymerised with hydrophobic water insoluble monomer. Suitable hydrophobic ethylenically unsaturated monomers are hydrocarbon monomers such as styrene and alkyl-substituted styrenes, alkyl acrylates and methacrylates (for instance methacrylate) and vinyl acetate.

The amount of hydrophobic monomer will generally be from 40 to 95% by weight, with the balance to 100% being the ionic monomer. However small amounts (e.g., up to 20%) of other monomers that are neither ionic nor hydrophobic may be included, example being vinyl pyrrolidone.

The matrix polymeric material can be made by solution polymerisation in the organic solvent or by oil-in-water emulsion polymerisation, followed by addition of sufficient alkali to solubilise the aqueous polymer in the conventional manner. Active ingredient can be dispersed or dissolved in the polymerising mixture before polymerisation, but preferably is dispersed or dissolved into a solution of the polymeric material after polymerisation. The polymer can be made as a water soluble salt by reverse phase polymerisation, e.g., in the hydrophobic oil that is used in the encapsulation process.

If the polymer was not formed as a reverse phase emulsion, the resultant solution of polymer containing active ingredient can be dispersed into the desired hydrophobic oil (or the polymer can be dispersed in the oil and the active ingredient then added) in the presence of suitable dispersion stabiliser that can be a water-in-oil emulsifier and/or an amphipathic polymeric stabiliser. Suitable emulsifiers, stabilisers and oils are described in, for instance, EP 128,661, EP 284,366 and EP 284,367. Emulsification can be achieved by homogenisation with a Silverson or other homogeniser.

The dispersion of aqueous polymer and active ingredient in oil can subsequently be subjected to distillation under reduced pressure until substantially all the water has been removed. If the active ingredient is temperature sensitive the reduced pressure should be sufficiently low that the distillation occurs at a safe temperature, for instance below 30° C. Anionic monomer is preferably present as ammonium salt, in which event the dispersion can be heated briefly to a temperature and for a time sufficient to drive off most of the ammonia but insufficient to damage any heat-sensitive active ingredient in the matrix polymer.

The resultant dispersion of dry polymer particles in oil can then be dispersed into an aqueous solution of coacervating polymeric material, for instance by emulsification using a Silverson homogeniser. The particle size can be controlled in known manner by appropriate selection of the emulsification conditions and generally is below 20 μm, usually below 10 μm, although if desired the process can be used to make larger particles, e.g., up to 100 μm or 500 μm. The size will usually be above 0.3 μm, e.g., up to 3 μm.

If the particle size of the resultant oil-in-water dispersion is small, each oil droplet may only contain one particle of matrix polymer, with the result that the core of the final product comprises a single matrix polymer particle surrounded by some oil. However each droplet, and therefore each core, often includes several matrix polymer particles dispersed in oil.

Coacervation can be by any known technique, for instance any of those mentioned or used in EP 356,239, but is preferably by use of "low critical solution temperature" (LCST) polymers. Coacervation can be brought about solely by heating as described in U.S. Pat. No. 3,244,640 but preferably coacervation is brought about by heating followed by the addition of a depressant. In particular, a process for encapsulating by coacervation particles each comprising matrix polymer (containing active ingredient) and an outer layer of oil can be performed as described in WO92/20441. This process comprises providing an aqueous solution of a LCST polymer that has a temperature of reversible insolubilisation (TRI) in that solution of T1, forming a dispersion of the particles in that solution at a temperature T2 that is below T1, heating the dispersion to a temperature above T1 and thereby precipitating the LCST polymer as a coacervate around the particles, then adding a TRI depressant to the solution and thereby reducing the temperature of reversible insolubilisation of the LCST polymer in that solution to a temperature T3 that is lower than T1, and either cooling the dispersion to a temperature between T3 and T1 and maintaining the dispersion at a temperature between T3 and T1, or separating the particles from the dispersion while at a temperature above T3.

The TRI depressant, and its amount, are selected to give the desired depression in the temperature of reversible insolubilisation. Preferably it is an electrolyte.

A wide variety of electrolytes can be used but since satisfactory results are obtained with simple inorganic salts it is generally preferred to use them as part or all of the electrolyte. Suitable salts include sodium, potassium, ammonium, calcium, magnesium and aluminium salts, particularly of carbonate, sulphate, chloride and nitrate. Some or all of the electrolyte can be anionic surfactant, for instance of the type conventionally present in a liquid detergent concentrate.

Typical amounts of salt that should be added are 2 to 30% based on the aqueous composition, or such as to give a 15:1 to 1:15 weight ratio of polymer:salt. The amount is preferably sufficient for T3 to be at least 5° C. below the anticipated lowest temperature of storage. As mentioned, some electrolyte can be present in the initial solution, typically in an amount of 0 to 5% based on the initial solution, provided this does not depress T1 too much.

Generally T1 is at least 5° C. higher than the anticipated temperature of usage, for instance the temperature of the dilution water into which the particles are to be dissolved.

Although we prefer to use an electrolyte for depressing the reversible insolubilisation temperature, any other material that has the desired depressant effect can be used. Generally them can all be characterised as being water-miscible non-solvents (in the absence of significant amounts of water) for the relevant LCST polymer. Examples include organic liquids such as lower alcohols, glycols and non-ionic surfactants. Particular examples are ethanol, glycerol, ethylene glycol, mono propylene glycol and ethoxylated octyl or nonyl phenol surfactants.

The LCST polymer can be a naturally occurring polymer such as certain cellulose derivatives, such as the methyl, hydroxy propyl, and mixed methyl/hydroxy propyl cellulose ethers. However it is generally preferred for the LCST polymer to be a synthetic polymer formed by polymerisation of what can be termed an LCST monomer either as a homopolymer or as a copolymer with a hydrophilic monomer that is present in an amount insufficient to cause T1 to be unacceptably high. Suitable LCST monomers include N-alkylacrylamide, N,N-dialkylacrylamide, diacetone acrylamide, N-acryloylpyrrolidine, vinyl acetate, certain (meth) acrylate esters (especially hydroxypropyl esters), styrene, and various other vinyl monomers, especially N-vinylimidazoline and the like.

When the LCST polymer is a copolymer, the comonomer is usually hydrophilic and can be non-ionic or ionic. Suitable non-ionic monomers include acrylamide, hydroxyethyl acrylate, vinyl pyrollidone, or hydrolysed vinyl acetate.

Anionic or cationic monomer can be used in place of or in addition to the non-ionic comonomer to form a copolymer or terpolymer with the LCST monomer respectively. Suitable anionic monomers include ethylenically unsaturated carboxylic or sulphonic acid monomers, for example (meth) acrylic acid and alkaline salts thereof, and 2-acrylamido methyl propane sulphonic acid. Suitable cationic monomers include dialkylaminoalkyl (meth)acrylates and acrylamides as acid addition or quaternary ammonium salts, for example dialkylaminoethyl (meth)acrylate acid addition salts. One beneficial effect resulting from the use of cationic or anionic comonomer or termonomer is that their presence can prevent the coagulation and subsequent phase separation of the encapsulated particles which may occur in particularly high salt environments such as may exist in certain detergents.

The method relies upon the reversible insolubilisation by temperature change of an LCST polymer to form a coacervate coating, followed by the addition of a TRI depressant to modify the properties of the coating in a beneficial manner. Since the initial insolubilisation is by temperature change, this can be conducted homogeneously throughout the composition and so can yield very uniform coacervation.

An essential modification of the coating is that the TRI depressant reduces the temperature of reversible insolubilisation of the coating. This means that the temperature of the solution can be cooled below the temperature at which the coacervate coating was first formed without the coating being solubilised. This permits handling, storage and recovery at ambient temperatures.

Another modification is that the addition of the TRI depressant can tend to change other physical properties of the coating of the LCST polymer. In particular, it is easily possible to select an LCST polymer that forms a much harder and less permeable coating in the presence of an added electrolyte (as the TRI depressant) than in its absence. Thus the addition of the electrolyte will generally both reduce the temperature of reversible insolubilisation of the polymer and will render the coating much harder and less permeable than it would be in the absence of the electrolyte.

However, the effect is reversible since when the concentration of TRI depressant is sufficiently reduced, the temperature of reversible insolubilisation will then rise again to, or at least towards, the initial temperature T1 of reversible insolubilisation. Also, if the TRI depressant hardened the coating, the coating may tend to revert to its original softer and more permeable texture.

The temperature T1 of reversible insolubilisation of the LCST polymer is the temperature at which the polymer will become insoluble if the solution containing the polymer is heated past T1 or will become soluble if insoluble polymer in that aqueous solution is cooled below that temperature. The temperature of reversible insolubilisation is generally reasonably abrupt, but may extend over a few degrees or more. Naturally T3 must be sufficiently low that any range for T1 does not significantly overlap the range for T3, which is the corresponding temperature for the polymer in the aqueous solution containing the TRI depressant. It should be noted that T1 and T3 relate to the polymer in the particular aqueous solution in which it exists. Thus, in the invention, the initial aqueous solution can contain some electrolyte or other TRI depressant in which event T1 in that solution will generally be lower than it would be if the initial solution had been free of electrolyte or other depressant, but additional electrolyte or other depressant is then added to reduce the temperature of reversible insolubilisation to T3.

T1 is generally at least 25° C. and often at least 30° C. and frequently is in the range 45° to 80° C. but can be as high as 100° C. Some polymers require the presence of some electrolyte in order to bring T1 in the initial solution down to a convenient value, e.g., below 100° C.

T3 is generally at least 5° C. lower than T1 and is preferably at least 10° C. and often at least 20° C. below T1. When the particles are to be stored in aqueous electrolyte, T3 should be below the probable storage temperature. Preferably T3 is 0° C., that is to say the coating will never dissolve in liquid water, but higher values of T3, such as 5° C. or even 10° C., can be acceptable in many instances.

Irrespective of how the coacervation of the shell is achieved, the choice of coacervate shell must be such as to allow eventual release of active ingredient from within the matrix when the product is exposed to selected conditions, whilst preventing release prior to that stage. For instance, if the particles are in the form of dry powder the coacervate shell should reduce ingress of ambient moisture sufficient to prevent significant deactivation of the active ingredient but, upon exposure to dilution water or an appropriate chemical reagent (for instance dilute alkali) the shell should permit adequate permeation through the shell and from the matrix into the surrounding liquor.

When the composition is in the form of a dispersion in liquid, the shell should prevent permeation of that liquid through the shell but should be capable of permitting permeation when the liquid is changed, for instance when it is diluted. When, as is preferred, the composition is in the form of a liquid detergent in which the encapsulated particles are dispersed, the shell should be such as to prevent substantially permeation of the alkaline liquid through the shell but should be such as to permit permeation by wash water, often warm wash water, when the Liquid detergent is diluted in wash water.

Suitable coacervating polymers can be the LCST polymers mentioned above and the coacervating polymers that have previously been proposed for, for instance, the coacervate shell around enzyme particles, especially enzyme particles that are to be dispersed into a liquid detergent. Suitable materials are described in, inter alia, EP-A- 356239. Cross linked PVA is suitable.

A wide variety of active ingredients can be encapsulated by the described technique including dyes (for pressure sensitive paper), agricultural chemicals, perfumes, flavours, condiments, essential oils, bath oils, bleaching agents, and enzymes. Suitable agricultural chemicals are water insoluble pesticides (e.g. herbicides and insecticides) that would otherwise need to be formulated as, for instance, an emulsifiable solution in oil. The invention is of particular value when applied to the encapsulation of enzymes, and in particular detergent enzymes, i.e. enzymes of the type that are useful for inclusion in laundry or other detergent compositions.

When the particle size is small, e.g. below 20 μm, the particulate composition is generally provided as a dispersion in the liquid medium, for instance a liquid detergent. When the particle size is larger, for instance above 50 μm and especially above 100 μm, the particles can be recovered as dry particles.

The liquid or dry composition can be substantially storage stable due to the protection provided by the matrix polymer, the oil layer and the encapsulating coacervate shell. Upon mixing with water, or other appropriate change in the ambient conditions, the outer shell disintegrates or swells sufficient to allow penetration of the oil layer and release of the active ingredient from within the matrix, possibly after chemical reversion of that matrix to render it more hydrophilic. For instance, if, as is preferred, the matrix polymer is the acid form of an anionic polymer, exposure to alkaline wash water will tend to solubilise it.

Suitable proportions of active ingredient: matrix polymer are 1:100 to 1:0.5 on a dry weight basis, whilst the matrix/active ingredient:coacervate polymer ratio is generally from 1:60 to 5:1 on a dry weight basis. The amount of oil encapsulated within the particles is generally from 20 to 97% based on the dry weight of the particles.

When the active ingredient is an enzyme for detergents and the composition is a liquid detergent, its formulation can be conventional for enzyme-containing liquid detergents except that the enzyme is included in the form of the described particles. Typical liquid detergents comprise, in % by weight,

| Component | Soap Built | Citrate Built |
|---|---|---|
| Linear alkyl benzene sulphonate | 10 | 10 |
| Alkyl ether sulphate | 2 | 4 |
| Soap | 14 | 1 |
| Alcohol ethoxylate | 13 | 6 |
| Sodium hydroxide (Triethanolamine) | 2(5) | 1(0) |
| Sodium xylene sulphonate | 1 | 5 |
| Sodium sulphate | 0 | 1 |
| Sodium carbonate | 0 | 2 |
| Tri-sodium citrate | 1 | 6 |
| Ethanol | 5 | 1 |
| Monopropylene glycol | 3 | 3 |
| Water | 44 | 60 |

When optimum stability is required, it is desirable that the active ingredient should not crystallise during the formation of the core, for instance during evaporation of water. Crystallisation with the core appears to tend to damage the integrity of the polymer shell around the core. Preferably therefore the core is a fluid core or a solid, non-crystalline, glass core. This is of particular value when the active ingredient is a water soluble agrochemical.

In one process of the invention, the active ingredient preferably is crystallisable and is in fluid form during coacervation, but does not subsequently crystallise within the shell. This seems to be desirable as the step of crystallisation appears to tend to disrupt the shell, and thus reduce the stability of the final product.

If the active ingredient is a crystallisable solid, it can be held in fluid form as a result of the core being in the form of a solution of the active ingredient in a solvent. In one process this solvent is retained in the particles so as to maintain the core fluid. For this purpose the solvent is preferably less volatile than water, so as to facilitate its retention in the core, and is used in an amount sufficient to maintain the core in fluid form at the end of the process. This fluid form may be a solution of the active ingredient in the solvent or it may be a melt whose melting point is held below ambient temperature as a result of the presence of the solvent. Suitable solvents for this purpose are aromatic hydrocarbons or other non-volatile solvents. The amount of the solvent is often 0.1 to 1.5, frequently 0.2 to 0.5, parts per part by weight active ingredient. The amount of solvent is preferably less than the amount of active ingredient.

The use of a non-volatile solvent is of particular value in the coacervation of trifluoralin.

Instead of forming the dispersion from a liquid composition of the active ingredient in a non-volatile solvent, it may be formed in a volatile solvent and this solvent may be evaporated by distilling the dispersion, thereby solidifying the core. Alternatively the dispersion formation may be conducted while the active ingredient is molten.

We find that it is particularly preferred that the core should not crystallise during any solidification stage involved in the formation of the product after coacervation, i.e., the solid core should have a glass structure. It seems that if the core crystallises this imposes strains and distortions on the coacervate shell leading to loss of stability on storage, but if the core solidifies as a glass then it conforms to the coacervate shell and does not destabilise it. Some molten active ingredients and solutions of active ingredients in solvent will solidify as a glass but many of the relevant active ingredients have a tendency to crystallise when being solidified from a melt or solution. Crystallisation can be prevented, and a glass structure achieved, by inclusion of sufficient of a matrix polymer in the core. The matrix polymer may be formed by polymerisation of polymerisable materials from solution within the core but preferably the core is initially formed as a solution of the matrix polymer and active ingredient in a solvent, and the solvent is evaporated by distillation of the dispersion so as to solidify the matrix polymer. If the amount of matrix polymer is insufficient, the core will crystallise but simple experimentation can be conducted to determine the minimum amount of matrix polymer that needs to be present in the core to prevent crystallisation. Generally the amount of matrix polymer needs to be at least 20%, and often at least 50%, by weight of the mixture of the matrix polymer and active ingredient.

The particles can be relatively large but are preferably substantially all below 100 μm. For instance they may be from 10 to 100 μm, often around 20 to 50 μm, and may then be used as powders. For instance powdered insecticides that are to be dusted may have a size of around 30 μm and may be used for, for instance, cockroach control. However it is particularly preferred that the particles should be below 10 μm and should be present as a dispersion in water. This composition, or a composition made by dilution in water, can be a sprayable composition.

In another aspect of the invention, the aqueous composition which has substantially all the particles below 10 μm in size is made by providing a first aqueous solution of a first water soluble coacervating polymer, providing a second aqueous solution of a second water soluble coacervating polymer that can interact with the first polymer to form the coacervate upon mixing the first and second solutions to form a mixed solution, mixing the said first and second solutions to form the mixed solution, providing a water immiscible, fluid, phase comprising the active ingredient, emulsifying this fluid phase into the mixed solution in the presence of an oil-in-water emulsifier and allowing the first and second polymers to interact and thereby coat the emulsified particles of the fluid phase to form the said polymer coacervate shell around the fluid particles, wherein the coacervate particles have 90% (by weight) below 5 μm and preferably below 2 μm. By the invention it is easily possible to obtain a composition in which 90% of the coacervated particles are below 2 μm with 50% less than 1 μm, and preferably 90% of the particles are less than 1 μm, preferably with 50% of the particles being less than 0.7 μm.

The emulsifier is conveniently an anionic emulsifier, a non-ionic emulsifier or a blend of the two. A suitable material is sold under the trade name Tensiofix B7146. The amount of emulsifier typically is from 1 to 10% of active emulsifier based on the total weight of the dispersion of aqueous medium and emulsified liquid particles.

A preferred feature of the invention is that the polymeric shell formed by coacervation can stabilise the particles against agglomeration in the aqueous medium, and so this greatly facilitates the formation of a stable dispersion of the particles in water.

Accordingly, a composition according to the invention is dilutable with water to form a sprayable composition and comprises a substantially stable dispersion in an aqueous medium of particles that are substantially all below 10 μm in size and that comprise a core containing a water insoluble active ingredient surrounded by a shell that has been formed by coacervation from one or more water soluble coacervating polymers and that stabilises the particles against agglomeration in the aqueous medium.

Thus preferably the coacervating shell is a material that promotes the stability of the particles, as a result of which the coacervated particles have less tendency to settle out and agglomerate than would similarly sized particles of the active ingredient alone, in an otherwise identical aqueous medium. Thus, for the first time, the final product relies upon the coacervate shell to promote the stability of the final product that is to be stored and transported to the point of use, where it can be converted into a novel sprayable composition merely by dilution with water. This is therefore in contrast to processes such as those described in GB 1,507,739 where some initial stabilisation is achieved but the process that is conducted involves further reaction of the coacervate shell so as to form a relatively unstable dispersion from which the capsules could be separated relatively easily.

The dilutable concentrated agrochemical or other composition of the invention must be sufficiently stable that it either remains as a true dispersion during storage or, if settlement does occur, can easily be redispersed merely by stirring. The composition may include additional emulsifiers, dispersants or dispersion stabilisers, but preferably the amount of such materials is very much less, below half and preferably below one quarter, the amount that would be required to stabilise the dispersion in the absence of the stabilising coacervate shell. Preferably the composition is substantially entirely free of such materials although coacervating polymer is preferably dissolved in the solution.

Thus the coacervating shell may provide most, and preferably all, of the stabilising properties that are required.

The coacervate shell can be made by bringing the coacervating polymer or polymers out of solution by, for instance, mixing counterionic polymers that cause mutual insolubilisation either in the presence of dispersed active ingredient or with the subsequent addition of it. Such techniques are known from, for instance, GB 2,073,132.

In order that the coacervating shell can provide these properties, it is desirable for the shell to be ionically charged, so that the particles then repel one another as a result of the like ionic charges on them. Preferably the particles have a relatively high positive or, preferably, negative zeta potential. Thus the zeta potential is preferably greater than −30 mv, and often greater than −50 mv, for instance the zeta potential can be as high as −100 mv or even higher. This can be achieved by using sufficient of an ionically charged polymer that the ionic charges in the polymer impart the desired zeta potential to the particles, and preferably excess of the ionic polymer is dissolved in the aqueous medium, thus promoting mutual repulsion of the particles. Thus preferably the coacervating polymer or one of the coacervating polymers is anionic and the amounts of polymers that are used are such that the particles are rendered anionic and the aqueous medium has some of the anionic polymer in solution in it. The ionically charged polymer should contain a sufficiently high proportion of ionic groups to impart the desired ionic charge to the particles.

The ionic polymer that contributes to the charge of the particles needs to be relatively hydrophilic in order that it gives good dispersing properties but this conflicts with the requirement that it shall come out of solution as a coacervate coating. A preferred way of insolubilising the anionic polymer so as to form a coacervate while still leaving the polymer with hydrophilic properties, is to coacervate it with a non-ionic or, preferably, cationic polymer that has characteristics such that it can interact with the anionic polymer to form the coacervate around the hydrophobic active ingredient but without destroying the dispersing properties of the anionic polymer shell. Preferably the cationic polymer has a lower molecular weight than the anionic polymer and the anionic polymer should be present in a molar excess, that is to say there should be a significantly larger number of anionic groups than cationic groups.

In order that the anionic polymer is hydrophilic, it is preferred to make it from a water soluble ethylenically unsaturated monomer or monomer blend that includes carboxylic or other anionic monomer. Preferably a 20:80 to 80:20 blend of acrylamide and (meth) acrylic acid (usually as sodium salt) is used. The lower molecular weight cationic polymer can be made from water soluble ethylenically unsaturated monomer or monomer blend that includes cationic polymer, a condensation polymer, most preferably a cationised urea formaldehyde or melamine formaldehyde polymer.

Suitable blends of molecular weight can be identified by experimentation, but generally the cationic polymer should have a molecular weight of below 100,000 and in practice the molecular weight should normally be below 50,000 and often below 10,000, while the anionic polymer will normally have a molecular weight above 100,000 and in practice often above 200,000, and up to 1 to 2 million although higher molecular weights can sometimes be used. At least one of the polymers (generally the anionic) can be amphoteric provided this does not prevent the desired formation of a stabilising coacervate.

What seems to be happening is that several molecules of cationic polymer become ionically bonded to parts of an anionic polymer chain so as to render those parts where charge neutralisation occurs more hydrophobic, thus attracting those parts to the hydrophobic active ingredient. The remainder of the anionic polymeric chain remains hydrophilic, thus promoting a high negative zeta potential and good stabilisation properties in an aqueous medium that includes an aqueous solution of the anionic polymer or of some other similar anionic polymer.

Suitable polymeric materials are described in, for instance, DE-A-3,545,803, GB 2,073,132, and 1,507,739 and U.S. Pat. No. 4,100,103.

The coacervate polymeric coating generally provides at least 10% and often at least 20% by weight of the dry weight of the particles but it is usually unnecessary for it to provide more than 50%, and usually it provides less than 40% of the dry weight of the particles. The content of active ingredient in the aqueous concentrate typically is in the range 5 to 20% by weight based on the concentrate.

In sprayable, dilutable or other stable aqueous dispersions of the invention, at least 90% by weight of the particles should be below about 10 μm in size since it will be very difficult to achieve adequate stabilisation if a significant proportion of the particles are above about 10 μm, and preferably at least 95% by weight are below 10 μm. Preferably at least 90, and usually at least 95%, by weight are below 5 μm. At least 50% are preferably below 3 μm. The coacervation is preferably conducted so as to make particles that initially have this size, but if necessary the coacervated material can be stirred or milled so as to break agglomerates down to the desired particle size.

The active ingredient can be any material that it is desired to provide in particulate form. For example, it can be an enzyme, but preferably it is an agriculturally useful material such as a semiochemical, nutrient or plant growth regulator or, preferably, a herbicide or pesticide. Suitable pesticides include insecticides, fungicides, nematocides, and biocides. Other suitable active ingredients that can usefully be incorporated into the particulate compositions of the invention include, for instance, perfumes, fragrances, pharmaceuticals and veterinary materials. Preferred active ingredients are chlorpyriphos, chlorpyriphos methyl, and trifluralin.

Although the invention is primarily of value for the production of agrochemical compositions that are stable dispersions that can be diluted with water, it is possible to apply the same coacervation technique to the production of other agrochemical particulate compositions.

Accordingly, another aspect of the invention is directed to a composition that comprises particles that comprise a core comprising a water insoluble agrochemical surrounded by a shell that has been formed by coacervation as described above, preferably by means of a low molecular weight water soluble cationic polymer with a molar excess of a higher molecular weight water soluble anionic polymer. These compositions can be, for instance, powders obtained by separating the coacervated particles from the described aqueous dispersion, followed by drying. The resultant powders can be used as such or can be made into granules or other larger particles, and will have the advantage that they will be readily dispersible into water.

In order to perform the coacervation process, it is necessary to provide a dispersion of the active ingredient in the desired particulate form, and conventional methods of providing such a dispersion, and conducting the coacervation, tend to be unsatisfactory with many of the agrochemicals and other active ingredients with which we are preferably concerned, even though the methods may be satisfactory for inks. Accordingly, we have developed two methods of particular value in the invention.

When the active ingredient is a solid that melts at below 80° C. (often below 50° C.), the process preferably comprises melting the active ingredient, dispersing it into the aqueous medium at a temperature at which it remains molten and under conditions to generate particles of the desired size (substantially all below 10 µm), coating the resultant dispersed particles by the coacervation process, and cooling the particles. This cooling may occur before the coacervation but after the dispersion stage, but often occurs during or, preferably, after the coacervation. After cooling, the particles are at a temperature below the melting point of the active ingredient.

Another convenient way of performing the process on many agrochemicals and other suitable active ingredients comprises dispersing the active ingredient into the aqueous medium while the active ingredient is present as a solution in an organic solvent that is more volatile than water, and thereby forming particles substantially all below 10 µm. The dispersed particles are then coated by the coacervation step while dispersed in the aqueous medium, and the resultant dispersion is then distilled to remove the organic solvent. If the active ingredient is crystallisable, then it is preferred that polymeric matrix or other material is included in the core with the active ingredient to prevent crystallisation when sufficient of the volatile solvent has been evaporated that crystallisation would otherwise have occurred. For instance some non-volatile solvent can be included to hold the material in solution, or polymeric matrix may be included in an amount sufficient to prevent crystallisation.

This technique of coacervating around a solution in volatile solvent and then distilling off the volatile solvent is of general applicability to the production of a wide range of active ingredients and so, according to another aspect of the invention a process for making a particulate composition comprises dispersing into an aqueous medium a solution of water insoluble active ingredient dissolved in an organic solvent that is more volatile than water, coating the resultant dispersed particles by coacervation of at least two water soluble coacervating polymers and thereby stabilising the particles against agglomeration while dispersed in the aqueous medium, and distilling the dispersion to remove the organic solvent.

It is possible to make relatively coarse particles, e.g., having an average size above 10 µm typically in the range 50 to 50 µm or even larger, by appropriate optimisation of the content of the aqueous solution and the manner of dispersing the organic solution of active ingredient into the aqueous solution. It is possible to separate these coarse particles from the aqueous medium in conventional manner and thus to form a dry particulate powder. Generally however the process results in the production of an aqueous dispersion as discussed above.

In this process, the active ingredient can be a liquid at room temperature (20° C.) but is generally a solid. It should be soluble in one or more organic solvents. The solution in the organic solvent is preferably a true solution but it can be a partial solution, for instance a dispersion being a dispersion that is stable in the absence of a dispersion stabiliser. The solubility of the active ingredient in the chosen solvent can be high or low, provided that it is not so low that it is impossible to achieve a solution of useful concentration.

The solvent that is used should be substantially water-immiscible in order that it will emulsify or disperse (rather than dissolve) into the aqueous medium. The dispersion can be achieved by mixing the solution into the aqueous medium under shear using, for instance, a Silverson mixer or other suitable emulsifier or homogeniser apparatus.

The solvent should be significantly more volatile than water and should have a boiling point substantially below the boiling point of water. For instance the solvent preferably has a boiling point below 70° C. and preferably between room temperature and 50° C. (at atmospheric pressure). Preferably the solvent forms an azeotrope with water so that the removal of solvent by distillation involves azeotropic distillation of substantially all the solvent with part only of the water of the aqueous medium.

Suitable solvents include any of the relatively low boiling water-immiscible organic solvents. The solvent is normally a hydrocarbon or halogenated hydrocarbon, the hydrocarbon generally being aliphatic or cycloaliphatic. Methylene chloride is particularly preferred.

Generally the coacervate coating is substantially complete before the product is distilled, but in some instances it can be desirable to rely upon the heating (that is supplied to cause distillation) also causing or completing the coacervation process.

The evaporation can be conducted by distillation at atmospheric or reduced pressure and is generally conducted as an azeotropic distillation. This is generally conducted under reduced pressure. By appropriate selection of the solvent and the pressure at which distillation is conducted it is possible to effect the distillation at low temperatures, e.g., as low as 50 ° C. or even as low as 30° C., and this is very advantageous if the active ingredient is sensitive to elevated temperatures, for instance being thermally unstable or volatile.

The distillation is preferably continued until the amount of solvent remaining is so low that the resultant composition, even after storage in a closed container, does not have a measurable flash point. Even if some solvent does remain (e.g., 2–30% based on active ingredient and total polymer), the amount is preferably as low as possible so as to maximise the solids content of the composition and to minimise environmental problems due to the solvent.

When, as is often preferred, the final product is to be an aqueous dispersion, the distillation conditions must, of course, be such as to remove the solvent whilst allowing sufficient of the aqueous phase to remain. Generally the amount of water in the distilled product is at least 30% and often at least 50%. Solids contents in the range 20% to 60% are suitable.

The coacervate shell can be a discontinuous stabilising shell, for instance a particulate shell of the type formed in DE 3,545,803, but preferably the shell is a substantially continuous polymeric coating. We have found that the polymeric coating formed by coacervation does not provide a serious impediment to satisfactory rates of release of the active ingredient to the pest or plant where the desired effect is to be achieved. However in some instances it is desirable to modify the capsules so as to regulate the rate of release.

Whereas it is preferred, from the stabilisation point of view, that the shell of the polymer particles in the dispersion should be the unreacted shell formed by coacervation, it can be desirable to subject the polymer in the shell to further reaction, provided this does not seriously impair the stabilisation properties of the shell. Thus although the shell preferably contains all the unreacted anionic groups initially present at the end of the coacervation process, if desired some of these can be further reacted so as to modify the properties of the shell. For instance they can be subjected to cross-linking with further urea formaldehyde or melamine formaldehyde resin as described in GB 1,507,739 or 2,073, 132. This will increase the strength of the shell but will reduce the stability of the dispersion and a better way of controlling the rate of release is for the core of the particles to comprise a polymeric matrix through which the active ingredient is distributed. The polymeric matrix should be water insoluble.

According to a another aspect of the invention, a particulate composition comprises particles having a core and a polymeric coating formed by coacervation from at least two water soluble coacervating polymers, and the core comprises a water-insoluble matrix polymeric material and a water-insoluble active ingredient. Preferably the particles are below 10 μm in size, as discussed above, and the composition is a stable dispersion in water. The active ingredient may be distributed substantially throughout the matrix either as a dispersion or solution in the polymer.

Although the composition can be made by coacervation around, for instance, pre-formed solid particles of the core, it is, as explained above, preferred to form the polymeric coacervate coating around fluid particles. It is possible for the core to remain in the fluid state and this is preferred when the active ingredient is crystallisable. However sometimes it is preferred that the core should be in solid form and should be substantially free of organic solvent, and it is then preferred for the active ingredient to be distributed throughout a solid polymeric matrix that is present in an amount sufficient to prevent crystallisation.

Preferably the active ingredient and any matrix polymeric material (or material that is a precursor of that) are both soluble in an organic solvent that is more volatile than water and the dispersion is made by the solvent process described above. In this type of process, the polymer can be one that is, for instance, a dispersion that is stable in the absence of a dispersion stabiliser in the chosen solvent for the active ingredient or can be a polymeric material that has been formed by reaction in the particles from precursor material that is soluble in the chosen solvent, i.e., the precursor for the matrix polymer must be soluble in the solvent.

When the particles are being made by the melting technique described above then the matrix polymer must be molten at the chosen temperature or must be made from a precursing material that will polymerise during or after dispersing the particles in the aqueous medium.

It is often desirable to make the matrix polymer particles by dispersing precursor, polymerisable material and the active ingredient in the aqueous medium and then causing polymerisation or cross linking.

The precursor material can be monomeric or other low molecular weight material but is preferably polymeric. Thus the reaction of the precursor polymer to form the matrix polymer may be, for instance, cross linking or graft polymerisation. When the solvent process is used, the matrix polymer in the final particles is preferably substantially unchanged chemically from the polymer that is dissolved into the initial solution of active ingredient and organic solvent.

The matrix polymer in the sprayable agrochemical compositions is normally selected such that the core is not only insoluble in the aqueous medium but is also substantially unswollen by the aqueous medium. Suitable polymers are any of the vinyl (or allyl) addition polymers that can conveniently be made by oil-in-water polymerisation or solution polymerisation in an organic solvent of ethylenically unsaturated monomer or monomer blend that is insoluble in water. Preferred polymers are acrylic polymers formed from monomers that comprise alkyl (meth) acrylate, generally in an amount of 30 to 100%. Other monomers that can be included, generally in amounts of less than 70% and preferably less than 40%, include styrenes, acrylonitrile, vinyl halides and the other relatively hydrophobic monomers that conventionally can be included in acrylic oil-in-water emulsion polymerisation. The polymer is generally linear but chain branching or slight cross linking can sometimes be desirable and so cross linking agent may be included.

The preferred matrix polymer is formed from 50 to 100% (preferably 80 to 100%) alkyl (meth) acrylate, and 0 to 50% styrene. Percentages are by weight. The alkyl group generally contains 1 to 10, preferably 2 to 6, carbon atoms. Blends of alkyl (meth) acrylates may be used. Polymers of 80 to 100% isobutyl methacrylate are particularly suitable.

Preferably the matrix polymer has a glass transition point (Tg) of above −20° C. and generally above −5° C. It is normally preferred for the glass transition point to be below 100° C. and usually below 40° C. By appropriate choice of Tg, monomers, and the ratio by weight of polymer:active ingredient, it is possible to regulate the rate of release.

Preferably the matrix polymer is substantially non-ionic and preferably it is formed entirely from non-ionic material. This is desirable since it facilitates the performance of the manufacturing process and in particular it minimises the risk of undesirable interaction between the matrix polymer and the coacervating polymers. Thus the polymeric matrix should be substantially non-swelling in the aqueous medium, and chemically inert to the coacervating polymers. However it can be convenient for it to swell slightly when the pH is changed, for instance when it is introduced into a more alkaline environment than the aqueous medium in which it is formed. Thus the matrix polymer may include (meth) acrylic or other acid groups and may be in the substantially free acid and non-swollen form in the aqueous medium but may swell slightly when exposed to alkaline conditions, such as may exist in the soil or on a plant leaf, due to ionisation of the carboxylic groups.

Since the matrix polymer (or its precursor) and active ingredient initially are both dissolved in the same solution, they are present in intimate admixture in the final particles and the polymer provides a matrix for the active ingredient.

When polymeric matrix is present in the agrochemical or other sprayable compositions, it is generally present in an amount of at least 0.2 parts, preferably at least 0.5 parts, per part dry weight of active ingredient, but it is usually unnecessary for it to provide more than about 2, or at the most about 5, parts by weight of the active ingredient.

The aqueous concentrates and sprayable compositions can include conventional additives to improve the stability of the composition (for instance thickeners such as gums or other natural polymers or synthetic polymeric thickeners). It may include dispersants and/or wetters to facilitate its dilution to form a sprayable composition and to facilitate its subsequent spraying and adherence to plants, soil or other substrate to which it is sprayed.

An advantage of the aqueous agrochemical dispersions of the invention, is that a flowable agrochemical composition, containing particles of a second agrochemical active ingredient, can be blended into the composition. Thus it is possible for the first time to provide in a convenient and environmentally acceptable form a concentrate of two insoluble agrochemicals wherein at least one has physical properties such that it cannot be put into the form of a conventional flowable.

Instead of using the aqueous dispersion as a concentrate for forming a dilute agricultural spray, it can be used for other purposes. For instance the concentrate (or a diluted composition formed from it) may be applied by spraying or otherwise on to a granular or other carrier, for instance to make a dry particulate composition that can be spread as a dry powder. Another way of making a spreadable powder is by aggregating the particles of the dispersion and then drying the aggregates. These aggregates can then be spread as dry powder or can be dispersed into water, whereupon the aggregates will disintegrate.

Any of the coacervation techniques described are generally suitable for use with any of the active ingredients described.

The following are some examples.

EXAMPLE 1

Preparation of LCST Copolymer

Diacetone acrylamide (1 part) and acrylamide (0.4 part) were dissolved in 1% aqueous sodium acetate at pH 6.5 (4.2 parts). This solution was purged with nitrogen for 45 min in a lagged reaction vessel fitted with a mechanical stirrer.

Polymerisation was initiated by addition of 5% aqueous ammonium persulphate (500 ppm) followed by 5% aqueous sodium metabisulphite (500 ppm). The course of the reaction was monitored by recording the temperature. After 30 min, the temperature had risen from 20° C. to a constant value of 70° C.

The mixture had become white and opaque and more viscous. On cooling a pale yellow clear viscous solution (25%) of Polymer A resulted.

By measuring the onset of turbidity of a 10% aqueous solution of Polymer A, the lower critical solution temperature (or temperature of reversible insolubilisation), was found to be 30° C.

EXAMPLE 2

Savinase Plus Matrix Polymer Dispersion in Oil

An aqueous phase is formed by mixing 160 g 30% solution of a copolymer of styrene and ammonium acrylate with 140 g liquid Savinase preparation (12 g active protease enzyme, supplied by Novo-Nordisk A/S) and its pH is adjusted to 9.0).

The oil phase is formed by mixing 9 g polymeric inverse emulsifier, 12.7 g 60% amphipathic polymeric stabiliser, 107.9 g non-volatile hydrocarbon oil and 31.9 g volatile hydrocarbon solvent.

The aqueous phase is added to the agitated oil phase and then homogenised with a high shear Silverson mixer whilst maintaining the temperature of the emulsion below 40° C. After 30 minutes emulsification, extra 138.5 g of the volatile hydrocarbon solvent is added as a diluent.

The resultant emulsion is warmed to 30° C. and water/solvent mixture distilled under reduced pressure at a constant temperature about 30° C. The volume of water and solvent removed is monitored and distillation continued until no further water is collected in the distillate and then the temperature is allowed to rise to 110° C. under vacuum to remove remaining solvent. The dried dispersion is held at 100° C. for 15 minutes to drive off ammonia so as to render the matrix polymer insoluble in water.

The contents of the flask are cooled. The dispersion of Savinase plus polymer particles in oil (40% solids) is stable and having an average particle diameter of less than 1 μm.

EXAMPLE 3

Microencapsulation of Dispersion-in-oil Obtained in Example 1

The dried enzyme/polymer dispersion (33 parts) from Example 1 is added with high shear mixing to 100 parts 10% solution of Polymer A at pH 4 from Example 1.

The resultant smooth o/w emulsion is warmed in a water bath to 40° C. and held at this temperature for 15 min. Aqueous sodium sulphate (10%, 5 parts) is added and the mixture then allowed to cool slowly to 20° C. A stable microcapsule suspension in water is obtained having average particle size diameter of about 1 micron.

EXAMPLE 4

The Savinase dispersion in oil prepared as in Example 2 (40 parts) was mixed with gentle agitation into 400 parts of an aqueous solution of poly-(vinyl alcohol) (2%; 74% hydrolysed $M_n$25000) adjusted to pH4 with dilute hydrochloric acid.

This mixture of oily droplets (containing the dispersed particles of hydrophobised enzyme) was warmed to 42° C. over 15 mins and held at this temperature for a further 30 mins. The outer shell of coacervated poly(vinyl alcohol) which could be seen clearly under the microscope to surround the oil droplets (average particle size 300 micron) was dross-linked by addition of 1 part of 50% aqueous glutaraldehyde solution, pH adjusted to 3 by a few drops of concentrated hydrochloric acid and the mixture stirred gently for 5 h at 42° C.

The capsules produced by this method were recovered by sieving through a fine nylon mesh were physically strong and could be recovered in a dry form by aerial drying. An enzyme assay for protease activity after physical rupture of these capsules in dilute aqueous detergent at pH9 showed 88% of the protease activity present in the oil protease suspension from Example 2.

A modern heavy duty compact powder detergent was formulated. To one half of this powder detergent was added the capsules—containing Savinase as described above. Savinase 6.0T granules (Novo-Norsik A/S Denmark) were added to the other half of the powder detergent to give an equal protease activity.

Both enzyme containing formulations were subjected to an accelerated storage stability test by being placed in open jars at 37° C. and 70% relative humidity. Protease assays of both formulations showed there to be more than double the activity in the capsules formulation than in the one made with normal granulated Savinase 6.0T.

EXAMPLE 5

The process of Example 4 was repeated but to a smaller particle size and the microcapsules containing the Savinase were added to a soap built liquid detergent and accelerated storage stability tests performed at 30° C. compared with a control which contained unprotected Savinase at the same protease activity. After 15 days, the capsule containing liquid detergent contained 2.5 times the protease activity than the unprotected control.

EXAMPLE 6

Demonstration of Partitioning and Dissolution Characteristics

Using the azeotropic distillation process as described in Examples 1 and 2, a dispersion comprising a dispersed phase of a styrene/acrylic acid polymer in a paraffinic oil is prepared. A water soluble polymeric dye (blue dextran) is incorporated into the polymer particles at 0.5% wt as a marker.

An experiment is performed to see if the polymer particles would activate (i.e. partition into and dissolve in the aqueous phase) on contact of matrix polymer plus dye dispersion with water at two different pH values.

The dispersion (1 part) was added with high shear mixing to water (99 parts) at either pH4 or pH9. After 2 min mixing the turbid mixture was centrifuged with these results:

| pH | Observation | Conclusion |
|---|---|---|
| 4 | Blue colour associated with oily layer Solution clear colourless | No activation |
| 9 | Distinct blue solution with a trace of oil on surface | Activation |

Therefore it can be seen that under acidic conditions the matrix polymer remains water insoluble and the particles stay in the oil phase. Thus the polymer particles are considered to partition into the oil phase at pH4, which is the pH prevailing at the time the dry polymer-in-oil dispersion is mixed into the aqueous coacervating solution. However when exposed to dilute alkali at pH9 (e.g. as would apply after permeation of the coacervate shell in dilute laundry wash water), the matrix polymer dissolves and releases its active ingredient.

EXAMPLE 7

Preparation of an Aqueous Dispersion of Chlorpyrifos 120 g of a 100% polyisobutyl acrylate (as matrix polymer) and 120 g Chloropyrifos technical grade were dissolved in 520 g dichloromethane, to form Solution A.

168 g of a 20% solution of a copolymer of acrylamide/ sodium acrylate having molecular weight about 400,000 were dissolved in 600 g water (Solution B).

76 g of a 35% cationic urea/formaldehyde resin containing about 10 urea units and sold under the trade name BC777 was dissolved in 100 g water (Solution C).

Solution B was subjected to stirring by a Silverson stirrer. Solution C was added over 20 secs., stirring was continued for 30 secs., and then solution A was added over 30 secs. Stirring was continued for a further 40 secs., and defoamer was added. A white emulsion was obtained.

The stirred emulsion was subjected to distillation under reduced pressure at a maximum temperature of 45° C., until all the dichlormethane was removed.

After sieving through a nylon mesh, a stable aqueous dispersion of solid particles was obtained and had a solids content of 26.5% by weight. The Chlorpyrifos content of the product was 10.1% and the median particle size was 2.21 µm. The zeta potential of the dispersion was −110.4 mv.

The dispersion was stable on storage, and was diluted with water to give a 0.3% concentration of particles in the sprayable solution. Some pot-grown cauliflowers were sprayed with the solution while others (the controls) were left untreated. Some of the treated and controlled pots were innoculated with cabbage root fly eggs immediately while others were innoculated after 5, 10, 15 or 22 weeks, and the pots were then grown in an insectary whilst the cabbage root fly larvae pupated. The mean numbers of larvae and pupae in each pot were counted. The results were as follows.

| Week | 0 | 5 | 10 | 15 | 22 |
|---|---|---|---|---|---|
| Control-number | 5.0 | 9.6 | 5.4 | 5.7 | 0.3 |
| Sample-number | 0 | 0 | 0.1 | 0 | 0 |

This demonstrates that the active ingredient was effective both immediately and for a period of 22 weeks, the maximum useful life of the crop.

EXAMPLES 8, 9 AND 10

The process was repeated in a manner similar to Example 7 but varying amounts of matrix polymer: 0 g, 60 g, 240 g were added. In each case, a reasonably stable dispersion was obtained. However, the stability of Examples 9 and 10 was significantly higher than the stability of Example 8 and this is attributed to the fact that Example 8 contains no matrix polymer and the active ingredient is in crystalline form in the core, whereas in Example 9 (50% polymer matrix based on active ingredient) and Example 10 the polymer matrix is present in an amount sufficient to prevent the active ingredient forming a crystal within the core. Since the core is a non-crystalline solid it can conveniently be referred to as a glass.

EXAMPLE 11

Preparation of an Aqueous Dispersion of 1,7-Dioxaspiro (5,5) Undecane ('Spiroketal')

Spiroketal is the principle component of the sex pheromone of the Olive fly: Dacus oleae.

160 g of a 95:5 copolymer of methyl methacrylate:ethyl acrylate and 22.5 g Spiroketal were dissolved in 640 g dichlormethane to form Solution A.

Solution B and C were prepared as in Example 1.

The solutions A, B and C were mixed in a manner identical to Example 1.

The dichloromethane was removed by distillation under reduced pressure in the temperature range 40°–50° C.

The final product was a stable dispersion of white particles of <5 µm size.

EXAMPLE 12

This was identical to Example 11, except that the polyisobutyl acrylate of Example 7 was used in place of the 95:5 copolymer.

It was found that the rate of release of the spiroketal to the atmosphere was different in the two products.

EXAMPLE 13

Solutions B and C were made and mixed as in Example 7, and the mixed solution was then heated to 45° C. and 800 g molten Trifluralin (technical grade) was added at 45° C. and blended using a Silversen stirrer. The liquid was allowed to cool with gentle stirring and was then subjected to stirring with a Silversen stirrer until 90% of the particles were below 10 μm and 50% were below 5 μm. The product was a stable orange suspension containing 45% by weight Fluralin.

EXAMPLE 14

A conventional flowable containing 50% by weight Linuron was made by bead milling a mixture of 538 g Linuron (technical grade) 253 g water, 138 g monoethylene glycol, 69 g surfactant and 1 g antifoam, until the particle size of the flowable was 100% below 10 μm. 150 g of this flowable suspension was then mixed with 333 g of the Trifluralin suspension of Example 13 and 76 g water to give a stable suspension containing 300 g/l Trifluralin and 150 g/l Linuron.

EXAMPLE 15

A 3:1 mixture of Trifluralin:Shellsol A was found to form a stable solution at R.T.

The above solution was found to emulsify in water when mixed with the surfactant *Tensiofix B7416.

(*The Tensiofix product is a blend of anionic and non-ionic surfactants).

Solution A was formed by adding to 356.25 g molten Trifluralin (technical); 118.75 g Shellsol A, and 125 g Tensiofix B7416 and cooled to room temperature.

63 g of a 20% solution of a copolymer of acrylamide/sodium acrylate having M.W.≈400,000 was dissolved in 300 g water (Solution B).

38 g of a 35% cationic urea/formaldehyde resin containing about 10 urea units; sold under the trade name BC 777, was dissolved in 50 g water (Solution C).

Solution B was subjected to stirring by a Silverson stirrer. Solution C was added over 10 secs, stirring was continued for 15 seconds and then Solution A was added over 15 seconds. Stirring was continued over another 50 seconds.

The final product contained 35% Trifluralin and was stable for a minimum of 2 weeks at 54° C. 90% of the particles were less than 1 μm.

EXAMPLE 16

The preparation of the trifluralin product was carried out in exactly the same manner as in Example 15, except that the Tensiofix surfactant was omitted from Solution A.

The product in this case had 90% of the particles less than 10 μm with 50% less than 5 μm.

The stability of the product in Example 15 is much higher than the stability of the product in Example 16.

We claim:

1. A particulate composition that comprises particles having an anhydrous core comprising (a) a solid matrix polymer and an active ingredient distributed throughout the solid matrix polymer and (b) an outer protective coacervated polymer shell.

2. A composition according to claim 1 in which the shell is formed of a cross-linked polymer.

3. A composition according to claim 1 in which the shell is formed of polyvinyl alcohol.

4. A composition according to claim 1 in which the particles have a size above 50 μm and the composition is a powder.

5. A composition according to claim 1 in which the particles have a size substantially all below 30 μm and the composition is a stable composition of the particles dispersed in a liquid.

6. A composition according to claim 5 comprising a dispersion of the particles in water, and wherein the active ingredient is an agrochemical and the composition, or a diluted composition made by dilution in water, is a sprayable composition.

7. A composition according to claim 5 in which the active ingredient is a detergent enzyme and the matrix polymer is a cationic polymer.

8. A composition according to claim 7 in which the matrix polymer is a substantially water insoluble, free-base, amino polymer that can be solubilised by acid.

* * * * *